(12) United States Patent
Uellner et al.

(10) Patent No.: US 8,668,746 B2
(45) Date of Patent: Mar. 11, 2014

(54) TWO-PART HAIR COLOURING COMPOSITION

(75) Inventors: Martin Uellner, Darmstadt (DE); Alexander Meuser, Egelsbach (DE); Sandra Schmelz, Marktheidenfeld (DE); Diana Bauer, Darmstadt (DE)

(73) Assignee: KAO Germany GmbH, Darmstadt (DE)

( * ) Notice: Subject to any disclaimer, the term of this patent is extended or adjusted under 35 U.S.C. 154(b) by 0 days.

(21) Appl. No.: 13/995,417

(22) PCT Filed: Dec. 23, 2011

(86) PCT No.: PCT/EP2011/073976
§ 371 (c)(1),
(2), (4) Date: Jun. 18, 2013

(87) PCT Pub. No.: WO2012/089674
PCT Pub. Date: Jul. 5, 2012

(65) Prior Publication Data
US 2013/0305463 A1 Nov. 21, 2013

(30) Foreign Application Priority Data
Dec. 28, 2010 (EP) ..................................... 10016115

(51) Int. Cl.
*A61Q 5/10* (2006.01)
(52) U.S. Cl.
USPC ................ 8/405; 8/406; 8/435; 8/580; 8/606; 8/696

(58) Field of Classification Search
USPC ....................... 8/405, 406, 435, 580, 606, 696
See application file for complete search history.

(56) References Cited

U.S. PATENT DOCUMENTS

2010/0257677 A1* 10/2010 Miyabe et al. .................... 8/405

FOREIGN PATENT DOCUMENTS

| DE | 44 30 521 C1 | 12/1995 |
|---|---|---|
| EP | 0 763 355 A1 | 3/1997 |
| EP | 2 204 160 A1 | 7/2010 |

OTHER PUBLICATIONS

STIC Search Report dated Aug. 23, 2013.*
International Search Report mailed Dec. 13, 2012.

* cited by examiner

*Primary Examiner* — Eisa Elhilo
(74) *Attorney, Agent, or Firm* — Norris McLaughlin & Marcus PA

(57) ABSTRACT

Present invention relates to a two part coloring composition for hair with improved dyeing and conditioning properties of hair. The object of the present invention a two part hair dyeing composition consisting of Parts A and B which are mixed immediately before application onto hair wherein Part A is based on at least one hair dye and comprising further at least one amino acid surfactant and Part B is an aqueous composition and comprising at least one oxidizing agent and at least one cationic or cationizable surfactant, wherein parts A and/or B comprises additionally at least one oil.

14 Claims, No Drawings

TWO-PART HAIR COLOURING COMPOSITION

This application is a 371 application of PCT/EP2011/073976 filed Dec. 23, 2011, which claims foreign priority benefit under 35 U.S.C. §119 of European Application No. 10016115.7 filed Dec. 28, 2010.

Present invention relates to a two part colouring composition for hair with improved dyeing and conditioning properties of hair.

Dyeing is a common in hair dressing practice. Various dyeing compositions have been made available on the market either based on new dyestuffs with improved dyeing effects and/or giving possibility in achieving new colours or based on non-dyeing chemicals for better uptake of the dyestuffs and for leaving hair in a good condition. Despite the developments, there is still need for further improvements especially in reducing hair damage and leaving hair in a cosmetically acceptable status so that no additional composition for improving cosmetic properties of hair has to be used subsequently. It has especially been observed that multiple processed hair and hair with parts with various degree of damage is difficult to dye homogeneously and also gives problems in their cosmetic properties after dyeing. Hair cosmetic properties referred to are especially combability, elasticity, natural softness and feeling upon touching and bounce.

Based on the above, the aim of the present invention is to provide a dyeing composition with improved dyeing effect on hair and, which, at the same time, colours especially multiple processed hair and hair with parts with various degree of damage homogeneously and which also leaves hair in a cosmetically improved condition so that no additional composition must be used subsequently.

The inventors of the present invention have surprisingly found out that a two part hair dyeing composition consisting of Parts A and B which are mixed immediately before application onto hair wherein Part A is based on at least one hair dye and comprising further at least one amino acid surfactant and Part B is an aqueous composition and comprises at least one oxidizing agent and at least one cationic or cationizable surfactant, wherein parts A and/or B comprises additionally at least one oil, colours hair homogeneously and leaves hair in an excellently cosmetically acceptable status. It has especially been observed that two part hair dyeing composition of the present invention colours multiple processed hair and especially the hair with parts with various degree of damage homogeneously and leaves said hair in an excellently cosmetically acceptable condition. It has furthermore observed that with the dyeing compositions of the present invention long lasting colours are achieved which clearly means that colours achieved are stable to environmental influences such as light and washing.

Accordingly the first object of the present invention a two part hair dyeing composition consisting of Parts A and B which are mixed immediately before application onto hair wherein Part A is based on at least one hair dye and comprising further at least one amino acid surfactant and Part B is an aqueous composition and comprising at least one oxidizing agent and at least one cationic or cationizable surfactant, wherein parts A and/or B comprises additionally at least one oil.

With the term oil it is meant that the compound is liquid at room temperature and it does not form salt especially under alkaline conditions so that the fatty acids are not oils within the meaning of the present invention.

Preferably the Part A of the two part composition of the present invention is also an aqueous compositions and preferably comprises at least 40%, more preferably 50%, most preferably 60% and in particular 70% by weight water, calculated to total of the composition. In a further preferred embodiment of the present invention is at least one amino acid surfactant in Part A is an anionic surfactant.

The second object of the present invention is the use of dyeing composition of the present invention for dyeing homogeneously and conditioning hair.

The third object of the present invention is the process for dyeing hair wherein Part A and Part B of the two part compositions are mixed immediately before application and applied onto hair and processed for 1 to 45 min and rinsed off from hair.

The composition of the present invention is provided to the consumers preferably in kit and therefore further object of the present invention is a kit for dyeing hair comprising at least two compositions wherein one of the compositions is Part A according to the present invention and the other is Part B according to present invention.

Part A of the two part hair dye composition of the present invention comprises at least one hair dye which is selected from oxidative dyes and direct dyes which may be cationic, anionic and neutral. It should be noted that the direct and oxidative dyes are also suitably used in mixture.

In principal all oxidative dyes available for hair colouring purposes are suitable within the meaning of the present invention. As a rule, it is possible to incorporate any developing substances known in the sate of the art. Special mention is made of p-phenylenediamine, p-aminophenol and substituted p-phenylenediamines such as 2,5-diamino-toluene, 2-n-propyl or 2-ethyl-p-phenylenediamine, 2,6-di-methyl-p-phenylene-diamine, 2-(2,5-diaminophenyl) ethanol, 1-amino-4-bis-(2'-hydroxy-ethyl)amino-benzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene, pyrazole and the derivatives thereof such as 1-hydroxyethyl-4,5-diaminopyrazole, 3,4-diamino-5-hydroxypyrazole, 3,5-diaminopyrazole, 3,5-diaminopyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 3,5-diamino-1,2,4-triazole, 4-aminophenol and the derivatives thereof such as 4-amino-3-methylphenol, 2-chloro-4-aminophenol, 2,6-dichloro-4-aminophenol, 2,4-diamino-phenol, 2,6-dibromo-4-aminophenol, tetramino pyrimidines, triaminohydroxy pyrimidines, diaminomono- and -dihydroxy pyrimidines, aminotriazines, 5-amino salicylic acid and/or 1,2,4-triamino benzene or the water-soluble salts thereof.

Further suitable ones aminopyridines are 2,5-diaminopyridine, 2,3-diaminopyridine, 2,6-diaminopyridine, 3-amino-2-methyl amino-6-methoxypyridine, 2-dimethyl-5-aminopyridine, 2-dimethyl aminoethyl-3-hydroxypyridine, 2-amino-4,6-dimethylpyridine, 2-amino-3-hydroxypyridine, 3-amino-2(β-hydroxyethyl amino)-6-methoxy-pyridine, 2,6-dimethyl amino-5-aminopyridine, 2-di(hydroxyethyl) amino-5-aminopyridine, 2-hydroxyethyl amino-5-aminopyridine, 4-hydroxy-2,5,6-triaminopyrimidine and/or the water-soluble salts thereof.

Within the meaning of the present invention above mentioned developers can as well be present as a mixture of each other.

The total concentration of the dye precursors (developing substances) customarily ranges between 0.001 to 5%, preferably 0.01 to 4% and more preferably 0.05 to 3%, and most preferably 0.1 to 2% by weight, calculated to the total composition, whereby these figures are always related to the proportion of free base.

In a further embodiment of the present invention compositions comprise in addition to at least one oxidative dye precursor at least one coupling substance. As a rule any coupling substance customarily used in oxidative hair colouration area is suitable within the meaning of the present invention. Non-limiting coupling substances, are 5-amino-2-methylphenol, 2-methyl-5-hydroxyethylaminophenol, 2,4,-diamnophenoxyehanol, 2-amino-4-hydroxyethylaminoanisol, 2-methyl-5-amino-6-chlorphenol, 1,3-bis(2,4-diaminophenoxy)propane, 2-bis(2-hydroxyethyl)aminotoluene, 2-amino-5-methylphenol, resorcinol, 2-methyl-resorcinol, 4-chlororesorcinol, 2-amino-4-chlorophenol, 5-amino-4-methoxy-2-methylphenol, 2-aminophenol, 3-amino-phenol, 1-methyl-2-hydroxy-4-aminobenzene, 3-N,N-dimethyl aminophenol, 2,6-dihydroxy-3,5-dimethoxypyridine, 5-amino-3-methylphenol, 6-amino-3-methylphenol, 1,3-diamino-benzene, 1-amino-3-(2'-hy-droxyethylamino)benzene, 1-amino-3-[bis(2'-hydroxy-ethyl)amino]benzene, α-naphthol, 4,6-dichlororesorcinol, 1,3-diamino-toluene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxy benzene, 2,4-diamino-3-chlorophenol, 5-amino-2-methoxyphenol and/or 1-methoxy-2-amino-4-(2'-hydroxyethyl amino)benzene and/or 1,3-bis(2,4-diaminophenoxy) propane or the water-soluble salts thereof. One or more of the above mentioned coupler can also be used in a mixture.

In the hair dyeing compositions according to the invention, the coupling substance(s) as reaction partners of the developing substance(s) are present in approximately the same molecular proportions as the developing substances, i.e. in amounts from 0.001 to 5%, preferably 0.01 to 4% and more preferably 0.05 to 3%, and most preferably 0.1 to 2% by weight, calculated to the total composition, whereby these figures always relate to the proportion of free base.

Suitable direct dyes are selected from cationic, anionic, neutral dyes and mixtures thereof as available commercially from various suppliers and used mainly in semi-permanent hair coloration.

One of the suitable direct dyes is cationic dyes. Non-limiting examples are Basic Blue 6, Basic Blue 7, Basic Blue 9, Basic Blue 26, Basic Blue 41, Basic Blue 99, Basic Brown 4, Basic Brown 16, Basic Brown 17, Basic Orange 31, Natural Brown 7, Basic Green 1, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57 and Basic Yellow 87, and their salts such as chloride, methosulfate, bromide etc. and mixtures thereof.

Further suitable direct dyes are anionic dyes. Suitable non-limiting examples are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium, and their mixtures.

Further suitable dyes for colouring hair within the meaning of the present invention are those of neutral nitro dyes. Suitable non-limiting examples are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid, and their mixtures.

Plant dyestuffs may also be used as hair colorant within the meaning of the present invention for example henna (red or black), alkanna root, laccaic acid, indigo, logwood powder, madder root and rhubarb powder, etc.

It should be noted that the above dyestuffs are also suitable for use in mixture. In other words, cationic, anionic and nitro dyes are used in mixture within the meaning of the present invention. When using direct dyes of various categories, their compatibility must be taken into account.

Among the direct dyes cationic and nitro dyes are preferred ones. Most preferred ones are cationic direct dyes.

Concentration of direct dyes in the compositions of the present invention is within the range of 0.001 to 5%, preferably 0.01 to 4% and more preferably 0.05 to 3%, and most preferably 0.1 to 2% by weight, calculated to total composition.

The total concentration of hair dye is preferably in the range of 0.001 to 15%, preferably 0.01 to 10% and more preferably 0.05 to 7.5%, and most preferably 0.1 to 5% by weight, calculated to total composition.

Part A of the two part hair dye composition of the present invention comprises at least one amino acid surfactant. Preferably at least one amino acid surfactant is an anionic surfactant and selected from the ones according to the general structure

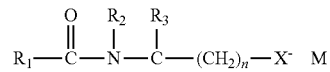

wherein $R_1$ is a saturated or unsaturated, straight or branched alkyl chain with 7 to 17 C atoms, $R_2$ is H or a methyl, $R_3$ is H, $COO^-M^+$, $CH_2COO^-M$ or COOH, n is 0 to 2, X is $COO^-$ or $SO_3^-$ and M is independent from each other H, sodium, potassium or ammonium.

With the term amino acid surfactants especially those surfactants are meant derived from taurate, glucamate, alanin or alaninate, sarcosinate and aspartate.

Suitably amino acid surfactant types are taurate, glutamate, alanin or alaninate, sarcosinate, aspartate surfactants, and mixtures thereof. Preferred are taurate, glutamate and sarcosinate surfactants and mixtures thereof. More preferred are taurates and glutamates and most preferred is glutamate type surfactants.

Suitable taurate surfactants are according to the general formula

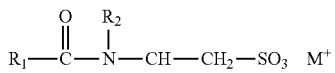

wherein $R_1$ is preferably a saturated or unsaturated, straight or branched alkyl chain with 7 to 17 C atoms, and more preferably 9 to 13 C atoms, $R_2$ is H or methyl, and M is H, sodium or potassium. Suitable examples are potassium cocoyl taurate, potassium methyl cocoyl taurate, sodium caproyl methyl taurate, sodium cocoyl taurate, sodium lauroyl taurate, sodium methyl cocoyl taurate, sodium methyl lauroyl taurate, sodium methyl myristoyl taurate, sodium methyl oleoyl taurate, sodium methyl palmitoyl taurate, and sodium methyl stearoyl taurate and mixtures thereof. Preferred are potassium cocoyl taurate, potassium methyl cocoyl taurate, sodium caproyl methyl taurate, sodium cocoyl taurate, sodium lauroyl taurate, sodium methyl cocoyl taurate and sodium methyl lauroyl taurate and mixtures thereof. More preferred are potassium cocoyl taurate, potassium methyl cocoyl taurate, sodium cocoyl taurate, sodium lauroyl taurate, sodium methyl cocoyl taurate and sodium methyl lauroyl taurate and mixtures thereof.

Suitable glutamate surfactants are according to the general formula

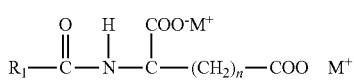

wherein $R_1$ is preferably a saturated or unsaturated, straight or branched alkyl chain with 7 to 17 C atoms, and more preferably 9 to 13 C atoms, and M is independent from each other H, sodium or potassium. Suitable examples are dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, and sodium undecylenoyl glutamate and mixtures thereof. Preferred are disodium capryloyl glutamate, disodium cocoyl glutamate, disodium lauroyl glutamate, potassium capryloyl glutamate, potassium cocoyl glutamate, potassium lauroyl glutamate, potassium myristoyl glutamate, sodium capryloyl glutamate, sodium cocoyl glutamate, sodium lauroyl glutamate, and sodium myristoyl glutamate and mixtures thereof. More preferred are disodium capryloyl glutamate, disodium cocoyl glutamate, disodium lauroyl glutamate, potassium capryloyl glutamate, potassium cocoyl glutamate, potassium lauroyl glutamate, sodium capryloyl glutamate, sodium cocoyl glutamate, and sodium lauroyl glutamate and mixtures thereof.

Suitable alanine or alaninate surfactants are according to the general formula

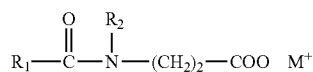

wherein $R_1$ is preferably a saturated or unsaturated, straight or branched alkyl chain with 7 to 17 C atoms, and more preferably 9 to 13 C atoms, $R_2$ is H or methyl and M is H, sodium or potassium. Suitable examples are cocoyl methyl β-alanine, lauroyl β-alanine, lauroyl methyl β-alanine, myristoyl β-alanine, potassium lauroyl methyl β-alanine, sodium cocoyl alaninate, sodium cocoyl methyl β-alanine and sodium myristoyl methyl β-alanine and mixtures thereof.

Suitable glycine surfactants are according to the general formula

wherein $R_1$ is preferably a saturated or unsaturated, straight or branched alkyl chain with 7 to 17 C atoms, and more preferably 9 to 13 C atoms, and M is H, sodium or potassium. Suitable examples are palmitoyl glycine, sodium lauroyl glycine, sodium cocoyl glycine, sodium myristoyl glycine, potassium lauroyl glycine, and potassium cocoyl glycine and mixtures thereof.

Suitable sarcosinate surfactants are according to the general formula

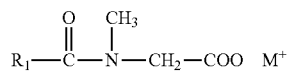

wherein $R_1$ is preferably a saturated or unsaturated, straight or branched alkyl chain with 7 to 17 C atoms, and more preferably 9 to 13 C atoms, and M is H, sodium or potassium. Suitable examples are potassium lauroyl sarcosinate, potassium cocoyl sarcosinate, sodium cocoyl sarcosinate, sodium lauroyl sarcosinate, sodium myristoyl sarcosinate, and sodium palmitoyl sarcosinate and mixtures thereof. Preferred are potassium lauroyl sarcosinate, potassium cocoyl sarcosinate, sodium cocoyl sarcosinate, and sodium lauroyl sarcosinate and mixtures thereof. More preferred are sodium cocoyl sarcosinate, and sodium lauroyl sarcosinate and mixtures thereof.

Suitable aspartate surfactants are according to the general formula

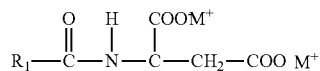

wherein $R_1$ is preferably a saturated or unsaturated, straight or branched alkyl chain with 7 to 17 C atoms, and more preferably 9 to 13 C atoms, and M is independent from each other H, sodium or potassium. Suitable examples are sodium lauroyl aspartate, sodium myristoyl aspartate, sodium cocoyl aspartate, sodium caproyl aspartate, disodium lauroyl aspartate, disodium myristoyl aspartate, disodium cocoyl aspartate, disodium caproyl aspartate, potassium lauroyl aspartate, potassium myristoyl aspartate, potassium cocoyl aspartate, potassium caproyl aspartate, dipotassium lauroyl aspartate, dipotassium myristoyl aspartate, dipotassium cocoyl aspartate, and dipotassium caproyl aspartate and mixtures thereof. Preferred are sodium lauroyl aspartate, sodium myristoyl aspartate, sodium cocoyl aspartate, and sodium caproyl aspartate and mixtures thereof.

It should be noted that compositions of the present invention can also comprise mixture of several type of amino acid surfactants such as mixture of glutamate and taurate surfactants, or mixture of taurate, glutamate and sarcosinate surfactants etc.

Concentration of at least one amino acid surfactant in the compositions of the present invention is in the range of 0.05 to 10%, preferably 0.1 to 7.5% and more preferably 0.1 to 5% and most preferably 0.2 to 2.5% by weight calculated to total of the composition.

Part B of the two part hair dye composition of the present invention comprises at least one oxidizing agent. Suitable oxidizing agents are hydrogen peroxide, urea peroxide, melamin peroxide or perborate salts. The most preferred is hydrogen peroxide. Concentration of at least one oxidizing agent is in the range of 0.1 to 20%, preferably 0.2 to 15%, more preferably 0.5 to 15% and most preferably 1 to 12% by weight, calculated to total of the composition.

Part B of the two part hair dye composition of the present invention comprises at least one cationic or cationizable surfactant. Preferred are selected from the compounds according to the general structures a and b which are:

a—

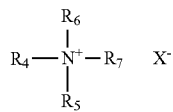

where $R_4$ is a saturated or unsaturated, branched or non-branched alkyl chain with 8-22 C atoms or

where $R_8$ is saturated or unsaturated, branched or non-branched alkyl chain with 7-21 C atoms and n has typical value of 1-4 or

where $R_9$ is saturated or unsaturated, branched or non-branched alkyl chain with 7-21 C atoms and n has typical value of 1-4, and
$R_5$ is unsaturated or saturated, branched or non-branched alkyl chain with 1-22 C atoms or

or

where $R_8$, $R_9$ and n are same as above.
$R_6$ and $R_7$ are lower alkyl chain with 1 to 4 Carbon atoms, and X is typically chloride, bromide, methosulfate, and
b—

wherein $R_{10}$ is a saturated or unsaturated, straight or branched alkyl group with 8 to 24 C atoms, $R_{11}$ is a straight or branched alkyl group with 1 to 4 C atoms, A is a group selected from O,

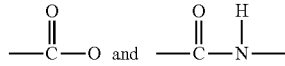

and B is selected from

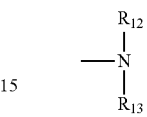

wherein $R_{12}$ and $R_{13}$ are the same or different is H or an alkyl with 1 to 4 C atoms, hydroxyl alkyl with 1 to 4 C atoms and di hydroxyl alkyl with 2 to 4 C atoms, and

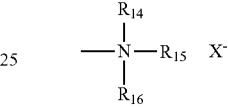

$R_{14}$, and $R_{15}$ are the same or different, an alkyl with 1 to 4 C atoms, hydroxyl alkyl with 1 to 4 C atoms and di hydroxyl alkyl with 2 to 4 C atoms, $R_{16}$ is an alkyl with 1 to 4 C atoms, hydroxyl alkyl with 1 to 4 C atoms or di hydroxyl alkyl with 2 to 4 C atoms or

wherein $R_{10}$, A and $R_{11}$ have the above meaning and X is chloride, bromide, methosulfate.

Compositions of the present invention comprise at least one alkyl ether alkyl amine or alkyl ether alkyl quaternary ammonium or alkyl ester/amide alkyl amine or alkyl ester/amide alkyl quaternary ammonium or alkyl quaternary ammonium according to the above general structures.

Non-limiting suitable examples are cetyl trimethly ammonium chloride, stear trimonium chloride, dipalmitoyl dimonium chloride, distearyl dimethyl ammonium chloride, stearamidopropyl trimonuim chloride, behentrimonium chloride, behenamidopropyltrimethylammonium chloride, dioleoylethyl dimethyl ammonium methosulfate, dioleoylethyl hydroxyethylmonium methosulfate stearyloxypropyl amine, palmityloxypropyl amine, stearyloxypropyldimethyl amine, stearyloxypropyldiethyl amine, stearyloxyethylyldimethyl amine, stearyloxyethyl amine, myristyloxypropyl amine, myristyloxypropyldimethyl amine, palmitamidopropyl amine, palmitamidopropyl methylamine, palmitamidopropyl diethylamine, palmitamidopropyl dibutylamine, palmitamidopropyl buylamine, palmitamidopropyl dipropylamine, palmitamidopropyl propylamine, palmitamidopropyl dihydroxyethylamine, palmitamidopropyl hydroxyethylamine, palmitamidopropyl dihydroxypropylamine, palmitamidopropyl hydroxypropylamine, lauramidopropyl amine, lauramidopropyl methylamine, lauramidopropyl diethylamine, lauramidopropyl dibutylamine, lauramidopropyl buylamine, lauramidopropyl dipropylamine, lauramidopropyl propylamine, lauramidopropyl dihydroxyethylamine, lauramidopropyl hydroxyethylamine, lauramidopropyl dihydroxypropylamine, lauramidopropyl hydroxypropylamine, stearamidopropyl amine, stearamidopropyl methylamine, stearamidopropyl diethylamine, stearamidopropyl dibutylamine, stearamidopropyl butylamine, stearamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, behenamidopropyl amine, behenamidopropyl methylamine, behenamidopropyl diethylamine, behenamidopropyl dibutylamine, behenamidopropyl butylamine, behenamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, dipalmitamidopropyl methylamine, dipalmitamidopropyl ethylamine, dipalmitamidopropyl butylamine, dipalmitamidopropyl propylamine, dipalmitamidopropyl hydroxyethylamine, dipalmitamidopropyl hydroxypropylamine, dilauramidopropyl amine, dilauramidopropyl methylamine, dilauramidopropyl buylamine, dilauramidopropyl hydroxyethylamine, dilauramidopropyl hydroxypropylamine, distearamidopropyl amine, distearamidopropyl methylamine, dibehenamidopropyl propylamine, dibehenamidopropyl hydroxyethylamine, palmitoamidopropyl trimethyl ammonium chloride, stearamidopropyl trimethylammonium chloride, behenamidopropyl tri hydroxyethalmonium chloride, distearylamidopropyl dimethyl ammonium chloride, dicetylamidodihydroxyethyl ammonium chloride, palmitoylpropyl amine, palmitoylpropyl methylamine, palmitoylpropyl diethylamine, palmitoylpropyl dibutylamine, palmitoylpropyl buylamine, palmitoylpropyl dipropylamine, palmitoylpropyl propylamine, palmitoylpropyl dihydroxyethylamine, palmitoylpropyl hydroxyethylamine, palmitoylpropyl dihydroxypropylamine, palmitoylpropyl hydroxypropylamine, myristoylpropyl amine, myristoylpropyl methylamine, myristoylpropyl diethylamine, myristoylpropyl dibutylamine, myristoylpropyl buylamine, myristoylpropyl dipropylamine, myristoylpropyl propylamine, myristoylpropyl dihydroxyethylamine, myristoylpropyl hydroxyethylamine, myristoylpropyl dihydroxypropylamine, myristoylpropyl hydroxypropylamine, stearoylpropyl amine, stearoylpropyl methylamine, stearoylpropyl diethylamine, stearoylpropyl dibutylamine, stearoylpropyl butylamine, stearoylpropyl dipropylamine, behenoylpropyl propylamine, behenoylpropyl dihydroxyethylamine, behenoylpropyl hydroxyethylamine, behenoylpropyl dihydroxypropylamine, behenoylpropyl hydroxypropylamine, behenoylpropyl amine, behenoylpropyl methylamine, behenoylpropyl diethylamine, behenoylpropyl dibutylamine, behenoylpropyl butylamine, behenoylpropyl dipropylamine, behenoylpropyl propylamine, behenoylpropyl dihydroxyethylamine, behenoylpropyl hydroxyethylamine, behenoylpropyl dihydroxypropylamine, behenoylpropyl hydroxypropylamine, dipalmitoylpropyl methylamine, dipalmitoylpropyl ethylamine, dipalmitylpropyl butylamine, dipalmitylpropyl propylamine, dipalmitylpropyl hydroxyethylamine, dipalmitylpropyl hydroxypropylamine, dilauroylpropyl amine, dilauroylpropyl methylamine, dilauroylpropyl buylamine, dilauroylpropyl hydroxyethylamine, dilauroylpropyl hydroxypropylamine, distearylpropyl amine, distearylpropyl methylamine, dibehenylpropyl propylamine, dibehenylpropyl hydroxyethylamine, palmitylpropyl trimethyl ammonium chloride, stearylpropyl trimethylammonium chloride, behenylpropyl tri hydroxyethalmonium chloride, distearylpropyl dimethyl ammonium chloride, dicetyldihydroxyethyl ammonium chloride, dioleoylethylhydroxyethylmonium methosulfate, and dicocoylethylhydroxyethylmonium methosulfate.

Concentration of at least one cationic or cationizable surfactant according to the above general structure in Part B of the two part hair dyeing composition is in the range of 0.01 to 10%, preferably 0.02 to 7.5%, more preferably 0.05 to 5% and most preferably 0.1 to 4% and in particular 0.2 to 3% by weight calculated to the total of the composition.

Part A and/or B of the two part hair dye composition of the present invention comprises at least one oil. Suitable ones are selected from synthetic and natural oils. Suitable synthetic oils are silicone oils either volatile or non-volatile ones such as volatile or non-volatile dimethicone, dimethiconol, polydimethylsiloxane, DC fluid ranges from Dow Corning, cyclosiloxanes such as DC 245 and arylated silicones such as diphenyl dimethicone, diphenylsiloxy phenyl trimethicone, tetramethyl tetraphenyl trisiloxane, triphenyl trimethicone, tetramethly tetraphenyl trisiloxane and trimethyl pentaphenyl trisiloxane. Synthetic oils include mineral oil such as paraffin oil and petrolatum. Further suitable synthetic oils are fatty acid esters such as isopropyl myristate, palmitate, stearate and isostearate, oleyl oleate, isocetyl stearate, hexyl laurate, dibutyl adipate, dioctyl adipate, myristyl myristate, oleyl erucate, cetyl palmitate, etc.

Nonlimiting examples to natural oils are such as argan oil, shea butter oil, olive oil, almond oil, avocado oil, ricinus oil, coconut oil, palm oil, sesame oil, peanut oil, whale oil, sunflower oil, peach kernel oil, wheat germ oil, macadamia nut oil, night primrose oil, jojoba oil, castor oil, or soya oil, lanolin, passiflora oil, black cumin oil, borage oil, grapeseed oil, macadamia oil, rosehip oil and hempseed oil.

The most preferred are argan oil, shea butter oil and paraffin oil. In the most preferred from of the invention, Part A comprises argan oil and/or shea butter oil and Part B comprises paraffin oil.

Concentration of at least one oil in the compositions of the present invention is in the range of 0.01 and 50%, preferably 0.1 to 40%, more preferably 0.5 to 35% and most preferably 1 to 30% and particularly 1 to 25% by weight calculated to total of the composition. The concentration ranges given here are valid for parts A and B separately and prior to mixing of the two compositions.

pH of the Part A varies in the range of 2 to 12, preferably 5 to 11, more preferably 6 to 10.5 and more preferably 6.8 to 10.5. In case a high lightening effect is looked for, i.e. lightened hair colour is 3 to 4 levels lighter than original hair colour, that high pH values must be preferred. It is the general knowledge of the skilled worker that at alkaline pH the lightening effect is also higher. Accordingly Part A comprises preferably at least one alkalizing agent, preferably selected from ammonia (or ammonium hydroxide) and a compound according to the following general structure

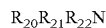

$R_{20}R_{21}R_{22}N$ wherein $R_{20}$, $R_{21}$ and $R_{22}$ are same or different H, $C_1$-$C_6$ alkyl, $C_1$-$C_6$ monohydroxyalkyl or $C_2$-$C_6$ polyhydroxyalkyl with the condition that at least one of $R_{20}$, $R_{21}$ and $R_{22}$ is a mono or polyhydroxyalkyl. Composition of the present invention comprises at least one alkalizing agent selected from the compounds according t general structure given above. In the preferred embodiment of the present invention, at least one alkanolamine is selected from compounds according to the above general structure wherein $R_{20}$, $R_{21}$ and $R_{22}$ are same or different H, $C_1$-$C_4$ alkyl, $C_1$-$C_4$ monohydroxyalkyl or $C_2$-$C_4$ polyhydroxyalkyl with the condition that at least one of $R_{20}$, $R_{21}$ and $R_{22}$ is a mono or polyhydroxyalkyl.

According to the most preferred embodiment of the present invention at least one alkanolamine is selected from compounds according to the above general formula wherein $R_{20}$, $R_{21}$ and $R_{22}$ are same or different H, $C_2$-$C_4$ alkyl, $C_2$-$C_4$ monohydroxyalkyl or $C_2$-$C_4$ polyhydroxyalkyl with the condition that at least one of $R_1$, $R_2$ and $R_3$ is a mono or polyhydroxyalkyl.

Suitable alkanolamines according to the general formula of above are monoethanolamine, diethanolamine, triethanolamine, monoethanol methylamine, monoethanoldimethylamine, di-ethanol/methylamine, monoethanolethylamine, monoethanoldiethylamine, diethanolethylamine, monoethanolpropylamine, monoethanoldipropylamine, diethanolpropylamine, monoethanolbutylamine and diethanolbutylamine.

Preferred are monoethanolamine, diethanolamine and triethanolamine. The most preferred is monoethanolamine.

The concentration of at least one alkanolamine in the compositions varies between 1 and 35%, preferably 1 and 30, more preferably 2.5 and 25 and most preferably 2.5 to 20% by weight calculated to the total composition.

Part B of the two part composition has an acidic pH and preferably in the range of 1 to 5, more preferably 2 to 4 and most preferably 2 to 3 and is adjusted with an organic and/or inorganic acid such as phosphoric acid and its salts.

Compositions of Part A and/or B of the present invention preferably comprise at least one thickening agent. Any type of thickening agent is suitable for the purpose of the present invention. Preferred are the nonionic ones such as cellulose and derivatives such as hydroxyethyl cellulose, methyl cellulose, xanthan gum and its derivatives, guar gum and its derivatives. Acrylate types of thickeners are also preferred as long as there is no compatibility issue with the polymer and the cationic and cationizable compounds. Suitable ones are acrylate which are especially suited for application in the alkaline pH and preferably comprises in the Part B in addition to a cationic and cationizable compounds.

According to the present invention compositions of Parts A and B can be in the form of emulsion, solution, dispersion, thickened liquid and/or gel. Emulsions are especially preferred. The compounds given in the following may suitably be comprised in Parts A and/or B unless otherwise disclosed.

Coloring composition of present invention can comprise additionally in the base formulation fatty acids with 0 to 3 ethylenic bonds and with fatty acyl chain length of 12 to 22 C atom. Concentration of the fatty acids can be in the range of 0.1 to 10%, preferably 0.1 to 7.5% and most preferably 0.2 to 5% by weight calculated to the total composition, prior to mixing with oxidizing agent. Non-limiting examples are myristic acid, palmitic acid, behenic acid, steraic acid, oleic acid, linoleic acid. The most preferred fatty acid is oleic acid.

Coloring composition of the present invention comprise at least one fatty alcohol or mixture of fatty alcohols with the chain length of 14 to 22 C atoms which may be straight or branched, saturated or unsaturated. Examples to suitable fatty alcohols, without limiting the choice, are myristyl alcohol, cetyl alcohol, stearyl alcohol, behenyl alcohol, oleyl alcohol and cetostearyl alcohol, octyldodecanol. The most preferred is cetostearyl alcohol well known with its trade name Lanette O or as Lanette N in mixture with sodium cetearyl sulfate from Cognis. Total fatty alcohol content should be in the range of 1 to 20% by weight, calculated to total composition prior to mixing with an oxidizing agent.

Colouring compositions according to present invention comprises surfactants selected from anionic, amphoteric (or zwiterionic) and/or cationic surfactants as emulsifier or solubilizer. Cationic surfactants are as well used as hair conditioners in the colouring composition.

The preferred non-ionic emulsifiers are ethoxylated fatty alcohols with an alkyl chain of 12 to 24 C atoms and with number of ethoxyl groups of 2 to 50, preferably 10 to 30. Examples are ceteth-20, ceteareth-30, palmeth-20, steareth-20, beheneth-20 etc. These compounds are named according to the fatty alcohol they are originating and number of ethoxyl groups is given at the end. These compounds are well known emulsifiers and found in any cosmetic ingredient book.

Further suited nonionic surfactants are, especially in mixture with fatty alcohol ethoxylates, for example, long-chain fatty acid mono- and dialkanolamides, such as coco fatty acid mono- or diethanolamide and myristic fatty acid mono or diethanolamide, stearic acid mono or diethanolamide.

Further nonionic surfactants suited again especially in admixture with fatty alcohol ethoxylates mentioned above are alkyl polyglucosides of the general formula

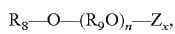

wherein $R_8$ is an alkyl group with 8 to 18 carbon atoms, $R_9$ is an ethylene or propylene group, Z is a saccharide group with 5 to 6 carbon atoms, n is a number from 0 to 10 and x is a number between 1 and 5.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates.

Further suitable nonionic surfactants are amineoxides. Such amineoxides are state of the art, for example $C_{12}$-$C_{18}$-alkyl dimethyl amineoxides such as lauryl dimethyl amineoxide, $C_{12}$-$C_{18}$-alkyl amidopropyl or -ethyl amineoxides, $C_{12}$-$C_{18}$-alkyl di(hydroxyethyl) or (hydroxypropyl) amineoxides, or also amineoxides with ethyleneoxide and/or propyleneoxide groups in the alkyl chain. Such amineoxides are on the market, for example, under the trade names "Ammonyx®" "Aromox®" or "Genaminox®".

Anionic surfactants suitable within the scope of the invention are in principal known from the cleansing compositions and may be present in an amount from 0.1 to about 10% by weight, calculated to the total composition prior to mixing with an oxidizing agent. Compatibility of anionic surfactant in the composition should be taken into account when choosing the type and the concentration.

These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates. Additional anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula

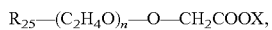

wherein $R_{25}$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula

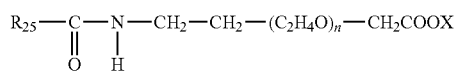

wherein $R_{25}$ and X have the above meanings, and n is in particular a number from 1 to 10, preferably 2.5 to 5.

Such products have been known for some time and are on the market, for example, under the trade name "AKYPO®" and "AKYPO-SOFT®".

Also useful are $C_8$-$C_{20}$-acyl isethionates, alone or in admixture with other anionic surfactants, as well as sulfofatty acids and the esters thereof.

As further surfactant component, the colouring compositions according to the invention can also contain amphoteric or zwitterionic surfactants, for example in an amount from about 0.5% to about 5%, preferably from about 1% to about 2.5% by weight, calculated to the total composition.

Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and—acetate have also proven suitable.

Form the above mentioned surfactants preferred are nonionic and anionic surfactants and their mixtures.

Total surfactant concentration is in the range of 0.5 to 15%, preferably 1 to 10%, more preferably 1 to 7.5% by weight calculated to total composition prior to mixing with an oxidizing agent.

Colouring composition can also contain cationic polymers as conditioning agents. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore, chitosan and chitin can also be included in the compositions as cationic natural polymers.

Furthermore, it has been found suitable those cationic polymers known with their CTFA category name Polyquaternium. Typical examples of those Polyquaternium 2, Polyquaternium 4, Polyquaternium 6, Polyquaternium 7, Polyquaternium 10, Polyquaternium 11, Polyquaternium 16, Polyquaternium 22 and Polyquaternium 28, Polyquaternium 30, Polyquaternium 37, Polyquaternium 36, Polyquaternium 46, Polyquaternium 67, Polyquaternium 87.

Typical concentration range for any of the cationic conditioners mentioned above can be 0.01-5% by weight, preferably 0.03-2.5% by weight and more preferably 0.05-1.5% by weight.

Hair dyeing composition of the present invention preferably comprise an organopolysiloxane wherein at least one silicium atom is linked to an alkylene group having a heteroatom, in particular a nitrogen atom, with a poly-(N-acyl alkyleneimine) units of the formula

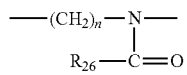

wherein n is a number from 1 to 5 and $R_{26}$ is hydrogen, a $C_1$-$C_{12}$-alkyl or cycloalkyl, aralkyl or aryl group.

Preferred organopolysiloxane polymers are those of the type disclosed in EP-A 640 643, in particular optionally quaternized aminoalkyl, in particular aminopropyl dimethyl polysiloxane/polyethyl oxazoline copolymers of the formula

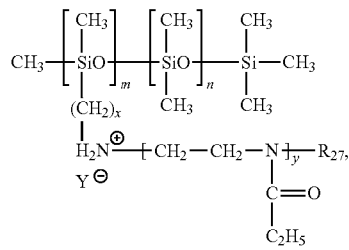

wherein m and n each are numbers from 20 to 10,000, in particular 50 to 7,000, especially 100 to 5,000, x is a number between 1 and 5, preferably 3, and y is a number from 5 to 30, $R_{27}$ is a $C_1$-$C_{12}$-alkyl or aryl group, in particular a methyl, ethyl or benzyl group, and $Y^-$ is an anion.

Especially suited are the organopolysiloxanes disclosed under the terms A-1, A-2 and A-3 on pages 12 to 13 of EP-A 640 643. The proportion of graft copolymers in the hair colouring compositions according to the invention ranges from 0.05% to 5%, preferably 0.1% to 2.5%, in particular 0.5% to 1.5% by weight, calculated to the total composition.

Coloring compositions according to the present invention can contain organic solvents as penetration enhancers and also as a solubilizers. Examples of such organic solvents are benzyloxy ethanol, benzyl alcohol, phenoxy ethanol, phenoxy isopropanol, methyl phenoxy ethanol, benzyl glycerol, N-benzyl formide, N-methylpyrrolidone, N-ethyl pyrrolidone, cinnamyl alcohol, phenethyl alcohol, p-methyl benzyl alcohol, butyl cellosolve, methyl carbitol, ethyl carbitol, propyl carbitol, butyl carbitol, diethyleneglycol, diethyl ether and dipropyleneglycol diethyl ether. Typically the concentration of those solvents can be in the range from 0.5% to 20%, preferably 0.5-15%, more preferably 0.5-10%, by weight calculated to the total composition, prior to mixing with oxidizing composition. Colouring compositions according to the invention may comprise thickening agents. These are, for example, the various cellulose derivatives such as hydroxyalkyl celluloses, e.g. hydroxyethyl cellulose, hydroxypropyl cellulose, hydroxypropyl methyl cellulose, natural polysaccharides such as xanthan gum; guar gum and the alkoxylation products thereof in amounts from 0.1-5%, preferably 0.1-3% and most preferably 0.1-2% by weight calculated to the total composition prior to mixing with oxidizing composition and depending on the desired consistency thereof.

Compositions may further comprise at least one ubiquinone of the formula

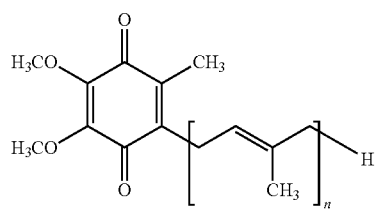

where n is a number between 1 and 10 at a concentration of 0.0001 to 1%, preferably from 0.0002 to 0.75%, more preferably from 0.0002 to 0.5% and most preferably from 0.0005 to 0.5% by weight, calculated to total composition, prior to mixing with oxidizing composition.

The composition comprises ubiquinone which is preferably selected from the ones where n is a number between 6 and 10 and more preferably it is ubiquinone 50 where n is 10, also known as Coenzyme Q10.

Composition can comprise at least one amino acid. At least one amino acid is comprised at a concentration of 0.01 to 10%, preferably 0.05 to 7.5% and more preferably 0.1 to 5% and most preferably 0.25 to 5% by weight calculated to total of each composition, prior to mixing with oxidizing composition.

Suitable amino acids are glycin, histidine, citrullin, asparagine, alanin, valin, leucin, isoleucin, pyrrolin, tryptophane, phenylalanine, methionine, serine, tyrosine, threonine and gluatamine. Preferably, the amino acid is selected from glycin, histidine, citrullin, asparagine, alanin, valin, leucin, isoleucin, pyrrolin, serine, tyrosine, threonine and gluatamine. More preferably, at least one amino acid is selected from glycin, histidine, asparagine, alanin, valin, leucin, pyrrolin, serine, tyrosine and gluatamine, and most preferably at least one amino acid is selected from glycin, asparagine, alanin, valin, leucin, and serine.

Composition can comprise further ceramide type of compound with the general formula

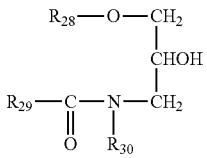

where $R_{28}$ and $R_{29}$ are independent from each other alkyl- or alkenyl group with 10 to 22 carbon atoms, $R_{30}$ is alkyl or hydroxyl alkyl with 1 to 4 carbon atoms group and n is a number between 1 to 6, preferably 2 or 3. Preferred compound according to the above chemical structure is cetyl-PG-hydroxyethylpalmitamide.

Further optional ingredient are sterols, especially the phytosterols as preferred hair restructuring agents. Especially preferred ones are of plant origin for example ergosterol, sitosterol, stigmasterol, fucosterol, brassicasterol, fungisterol, campesterol, zymosterol, ascosterol, cerevisterol, episterol, faecosterol, spinasterol. Among those phytosterols, the ones found in "Avocadin" which is the unsaponified fraction of the avocado oil is more preferred.

Following examples are to illustrate the invention but not to limit.

EXAMPLE 1

Part A

|  |  |
| --- | --- |
| Sodium cocoyl glutamate | 1.0 |
| Argan oil | 0.2 |
| Basic red 51 | 1.0 |
| Monoethanolamine | 8.0 |
| Water | q.s. to 100 |

The pH of the above composition is 11.00

Part B

|  | % by weight |
| --- | --- |
| Hydrogen peroxide | 6.0 |
| Cetrimonium chloride | 1.0 |
| Phosphoric acid | q.s. to pH 3.0 |
| Water | to 100 |

The above compositions were mixed 1:1 by weight and applied onto hair and after processing of 30 min at room temperature the composition was rinsed off from hair.

It was observed that hair was homogeneously coloured and easily combable and felt natural and soft upon touching. Removal of either amino acid surfactant or cationic surfactant resulted in loss of effects.

EXAMPLE 2

Part A

|  |  |
| --- | --- |
| Sodium cocoyl glutamate | 1.0 |
| Argan oil | 0.2 |
| Cetearyl alcohol | 5.0 |
| Ceteareth-20 | 2.0 |
| Toluene-2,5-diamine sulphate | 0.5 |
| 2-amino-3-hydroxypyridine | 0.5 |
| Monoethanolamine | 8.0 |
| Water | q.s. to 100 |

The pH of the above composition is 11.00

Part B

|  | % by weight |
| --- | --- |
| Hydrogen peroxide | 6.0 |
| Cetrimonium chloride | 2.0 |
| Paraffin oil | 5.0 |
| Cetearyl alcohol | 5.0 |
| Phosphoric acid | q.s. to pH 3.0 |
| Water | to 100 |

The above compositions were mixed 1:1 by weight and applied onto hair and after processing of 30 min at room temperature the composition was rinsed off from hair.

It was observed that hair was homogeneously coloured into a reddish violet shade and easily combable and felt natural and soft upon touching. The hair had natural elasticity and enhanced shine. Removal of amino acid surfactant and/or cationic surfactant and/or oils resulted in loss of effects.

EXAMPLE 3

Part A

|  |  |
| --- | --- |
| Sodium lauroyl glutamate | 2.0 |
| Argan oil | 0.2 |
| Shea butter oil | 0.2 |
| Cetearyl alcohol | 5.0 |
| Ceteareth-20 | 2.0 |
| Toluene-2,5-diamine sulphate | 0.5 |
| 1,3-bis(2,4-diamniophenoxy propane 4 HCl | 0.5 |
| Monoethanolamine | 8.0 |
| Water | q.s. to 100 |

The pH of the above composition is 10.50

Part B

|  | % by weight |
| --- | --- |
| Hydrogen peroxide | 6.0 |
| Cetrimonium chloride | 1.0 |
| Paraffin oil | 5.0 |
| Cetearyl alcohol | 5.0 |
| Ceteareth-20 | 1.0 |
| Phosphoric acid | q.s. to pH 3.0 |
| Water | to 100 |

The above compositions were mixed 1:1 by weight and applied onto hair and after processing of 30 min at room temperature the composition was rinsed off from hair.

It was observed that hair was homogeneously coloured into a blue shade and easily combable and felt natural and soft upon touching. The hair had natural elasticity and enhanced shine. Removal of amino acid surfactant and/or cationic surfactant and/or oils resulted in loss of effects.

EXAMPLE 4

Part A

| Sodium lauroyl glutamate | 2.0 |
| --- | --- |
| Argan oil | 0.2 |
| Shea butter oil | 0.2 |
| Cetearyl alcohol | 5.0 |
| Ceteareth-20 | 2.0 |
| Toluene-2,5-diamine sulphate | 0.5 |
| 2-amino-3-hydroxypyridine | 0.5 |
| Basic red 51 | 0.5 |
| Monoethanolamine | 8.0 |
| Water | q.s. to 100 |

The pH of the above composition is 10.50

Part B

|  | % by weight |
| --- | --- |
| Hydrogen peroxide | 6.0 |
| Steartrimonium chloride | 1.0 |
| Paraffin oil | 5.0 |
| Cetearyl alcohol | 5.0 |
| Ceteareth-20 | 1.0 |
| Phosphoric acid | q.s. to pH 3.0 |
| Water | to 100 |

The above compositions were mixed 1:1 by weight and applied onto hair and after processing of 30 min at room temperature the composition was rinsed off from hair.

It was observed that hair was homogeneously coloured into a red violet shade and easily combable and felt natural and soft upon touching. The hair had natural elasticity and enhanced shine. Removal of amino acid surfactant and/or cationic surfactant and/or oils resulted in loss of effects.

EXAMPLE 5

Part A

| Sodium lauroyl glutamate | 2.0 |
| --- | --- |
| Argan oil | 0.2 |
| Shea butter oil | 0.2 |
| Cetearyl alcohol | 5.0 |
| Ceteareth-20 | 2.0 |
| Toluene-2,5-diamine sulphate | 0.5 |
| 2-amino-3-hydroxypyridine | 0.5 |
| HC Blue 17 | 0.5 |
| Monoethanolamine | 8.0 |
| Water | q.s. to 100 |

The pH of the above composition is 10.50

Part B

|  | % by weight |
| --- | --- |
| Hydrogen peroxide | 6.0 |
| Stearoxypropyldimethyl amine | 1.0 |
| Paraffin oil | 5.0 |
| Cetearyl alcohol | 5.0 |
| Ceteareth-20 | 2.0 |
| Phosphoric acid | q.s. to pH 3.0 |
| Water | to 100 |

The above compositions were mixed 1:1 by weight and applied onto hair and after processing of 30 min at room temperature the composition was rinsed off from hair.

It was observed that hair was homogeneously coloured into a reddish violet shade and easily combable and felt natural and soft upon touching. The hair had natural elasticity and enhanced shine. Removal of amino acid surfactant and/or cationic surfactant and/or oils resulted in loss of effects.

EXAMPLE 6

Part A

| Sodium lauroyl glutamate | 2.0 |
| --- | --- |
| Argan oil | 0.2 |
| Shea butter oil | 0.2 |
| Cetearyl alcohol | 5.0 |
| Ceteareth-20 | 2.0 |
| 4,5-diamino-1-hydroxyethylpyrazol sulphate | 0.5 |
| 1-Naphtol | 0.5 |
| Basic red 51 | 0.5 |
| Monoethanolamine | 8.0 |
| Water | q.s. to 100 |

The pH of the above composition is 10.50

Part B

|  | % by weight |
| --- | --- |
| Hydrogen peroxide | 6.0 |
| Behentrimonium chloride | 1.0 |
| Paraffin oil | 5.0 |
| Cetearyl alcohol | 5.0 |
| Ceteareth-20 | 1.0 |
| Phosphoric acid | q.s. to pH 3.0 |
| Water | to 100 |

The above compositions were mixed 1:1 by weight and applied onto hair and after processing of 30 min at room temperature the composition was rinsed off from hair.

It was observed that hair was homogeneously coloured into a reddish violet shade and easily combable and felt natural and soft upon touching. The hair had natural elasticity and enhanced shine. Removal of amino acid surfactant and/or cationic surfactant and/or oils resulted in loss of effects.

Similar results were obtained with the following examples.

EXAMPLE 7

Part A

| | |
|---|---|
| Sodium cocoyl glutamate | 2.0 |
| Argan oil | 0.3 |
| Shea butter oil | 0.1 |
| Cetearyl alcohol | 5.0 |
| Ceteareth-20 | 2.0 |
| 4,5-diamino-1-hydroxyethylpyrazol sulphate | 0.5 |
| 1-Naphtol | 0.5 |
| Basic red 51 | 0.5 |
| Monoethanolamine | 8.0 |
| Water | q.s. to 100 |

The pH of the above composition is 10.50

Part B

| | % by weight |
|---|---|
| Hydrogen peroxide | 6.0 |
| Dioleoylethylhydroxyethylmonium methosulphate | 1.0 |
| Paraffin oil | 5.0 |
| Cetearyl alcohol | 5.0 |
| Ceteareth-20 | 2.0 |
| Phosphoric acid | q.s. to pH 3.0 |
| Water | to 100 |

EXAMPLE 8

Part A

| | |
|---|---|
| Sodium cocoyl glutamate | 2.0 |
| Argan oil | 0.3 |
| Shea butter oil | 0.1 |
| Behenyl alcohol | 2.0 |
| Cetyl alcohol | 2.0 |
| Ceteareth-20 | 2.0 |
| 4,5-diamino-1-hydroxyethylpyrazol sulphate | 0.5 |
| 1-Naphtol | 0.5 |
| Basic red 51 | 0.5 |
| Ammonium hydroxide (25%) | 8.0 |
| Water | q.s. to 100 |

The pH of the above composition is 10.50

Part B

| | % by weight |
|---|---|
| Hydrogen peroxide | 6.0 |
| Dioleoylethylhydroxyethylmonium methosulphate | 0.3 |
| Cetrimonium chloride | 0.1 |
| Behenamidopropyltrimonium chloride | 0.2 |
| Paraffin oil | 5.0 |
| Cetearyl alcohol | 5.0 |
| Ceteareth-20 | 1.5 |
| Phosphoric acid | q.s. to pH 2.5 |
| Water | to 100 |

EXAMPLE 9

Part A

| | |
|---|---|
| Sodium cocoyl glutamate | 2.0 |
| Argan oil | 0.3 |
| Shea butter oil | 0.1 |
| Behenyl alcohol | 2.0 |
| Cetyl alcohol | 2.0 |
| Ceteareth-20 | 2.0 |
| 4,5-diamino-1-hydroxyethylpyrazol sulphate | 0.5 |
| 1-Naphtol | 0.5 |
| Basic red 51 | 0.5 |
| Monoethanolamine | 8.0 |
| Water | q.s. to 100 |

The pH of the above composition is 10.50

Part B

| | % by weight |
|---|---|
| Hydrogen peroxide | 6.0 |
| Dioleoylethylhydroxyethylmonium methosulphate | 0.3 |
| Cetrimonium chloride | 0.1 |
| Behenamidopropyltrimonium chloride | 0.2 |
| Paraffin oil | 5.0 |
| Cetearyl alcohol | 5.0 |
| Ceteareth-20 | 1.5 |
| Phosphoric acid | q.s. to pH 2.5 |
| Water | to 100 |

The invention claimed is:

1. A two part hair dyeing composition comprising Parts A and B which are mixed immediately before application onto hair wherein Part A comprises at least one hair dye and at least one amino acid surfactant and Part B is an aqueous composition and comprising at least one oxidizing agent and at least one cationic or cationizable surfactant, wherein parts A and/or B comprises additionally at least one oil, wherein at least one amino acid surfactant on Part A is an anionic surfactant and selected from the surfactants according to general structure

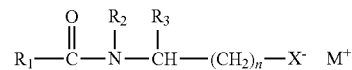

wherein $R_1$ is a saturated or unsaturated, straight or branched alkyl chain with 7 to 17 C atoms, $R_2$ is H or a methyl, $R_3$ is H, $COO^-M^+$, $CH_2COO^-M$ or $COOH$, n is 0 to 2, X is $COO^-$ or $SO_3^-$ and M is independently from each other H, sodium, potassium or ammonia.

2. The composition according to claim 1 wherein Part A is an aqueous composition comprising at least 40% by weight water, calculated to total of the composition.

3. The composition according to claim 1 wherein the hair dye in Part A is selected from oxidation dyes and cationic, anionic and neutral direct dyes.

4. The composition according to claim 1 wherein at least one amino acid surfactant in Part A is a glutamate surfactant and selected from the surfactants according to general structure

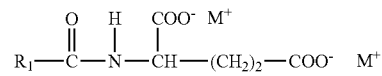

wherein $R_1$ is a saturated or unsaturated, straight or branched alkyl chain with 7 to 17 C atoms, and M is independent from each other H, sodium or potassium.

5. The composition according to claim 4 wherein amino acid surfactant in part A is selected from the group consisting of disodium capryloyl glutamate, disodium cocoyl glutamate, disodium lauroyl glutamate, potassium capryloyl glutamate, potassium cocoyl glutamate, potassium lauroyl glutamate, sodium capryloyl glutamate, sodium cocoyl glutamate, and sodium lauroyl glutamate and mixtures thereof.

6. The composition according to claim 1 wherein Part A has a pH in the range of 2 to 12 and comprises at least one alkalizing agent selected from ammonium hydroxide and a compound according to general structure $R_{20}R_{21}R_{22}N$ wherein $R_{20}$, $R_{21}$ and $R_{22}$ are same or different H, $C_1$-$C_6$ alkyl, $C_1$-$C_6$ monohydroxyalkyl or $C_2$-$C_6$ polyhydroxyalkyl with the condition that at least one of $R_{20}$, $R_{21}$ and $R_{22}$ is a mono or polyhydroxyalkyl.

7. The composition according to claim 1 wherein the oxidizing agent in Part B is hydrogen peroxide.

8. The composition according to claim 1 wherein the cationic or cationizable surfactant is Part B is selected from the compounds according to the general structures a and b which are:

a—

$$R_4-\overset{\overset{\displaystyle R_6}{|}}{\underset{\underset{\displaystyle R_5}{|}}{N^+}}-R_7 \quad X^-$$

where $R_4$ is a saturated or unsaturated, branched or non-branched alkyl chain with 8-22 C atoms or $R_7$ CO NH $(CH_2)_n$ where $R_8$ is saturated or unsaturated, branched or non-branched alkyl chain with 7-21 C atoms and n has typical value of 1-4 or $R_9$ CO O $(CH_2)_n$ where $R_9$ is saturated or unsaturated, branched or non-branched alkyl chain with 721 C atoms and n has typical value of 1-4, and $R_5$ is unsaturated or saturated, branched or non-branched alkyl chain with 1-22 C atoms or $R_8$ CO NH $(CH_2)_n$ or $R_9$ CO O $(CH_2)_n$ where $R_8$, $R_9$ and n are same as above, $R_6$ and $R_7$ are lower alkyl chain with 1 to 4 Carbon atoms, and X is typically chloride, bromide, methosulfate, and b—

$R_{10}$-A-$R_{11}$—B wherein $R_{10}$ is a saturated or unsaturated, straight or branched alkyl group with 8 to 24 C atoms, $R_{11}$ is a straight or branched alkyl group with 1 to 4 C atoms, A is a group selected from O,

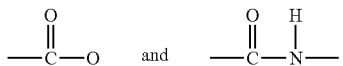   and and B is selected from $$-\overset{\overset{\displaystyle R_{12}}{|}}{\underset{\underset{\displaystyle R_{13}}{|}}{N}}$$

wherein $R_{12}$ and $R_{13}$ are the same or different is H or an alkyl with 1 to 4 C atoms, hydroxyl alkyl with 1 to 4 C atoms and di hydroxyl alkyl with 2 to 4 C atoms, and $$-\overset{\overset{\displaystyle R_{14}}{|}}{\underset{\underset{\displaystyle R_{16}}{|}}{N^+}}-R_{15} \quad X^-$$

$R_{14}$, and $R_{15}$ are the same or different, an alkyl with 1 to 4 C atoms, hydroxyl alkyl with 1 to 4 C atoms and di hydroxyl alkyl with 2 to 4 C atoms, $R_{16}$ is an alkyl with 1 to 4 C atoms, hydroxyl alkyl with 1 to 4 C atoms or di hydroxyl alkyl with 2 to 4 C atoms or

—$R_2$-A-$R_1$ wherein $R_{10}$, A and $R_{11}$ have the above meaning and X is chloride, bromide, methosulfate.

9. The composition according to claim 1 wherein the cationic and/or cationizable compound is selected from the group consisting of cetyl trimethly ammonium chloride, stear trimonium chloride, dipalmitoyl dimonium chloride, distearyl dimethyl ammonium chloride, stearamidopropyl trimonuim chloride, behentrimonium chloride, behenamidopropyltrimethylammonium chloride, dioleoylethyl dimethyl ammonium methosulfate and dioleoylethyl hydroxyethylmonium methosulfate stearyloxypropyl amine.

10. The composition according to claim 1 wherein Part A and Part B both comprise at least one oil selected from the group consisting of silicones, paraffin oil, fatty acid esters selected from the group consisting of isopropyl myristate, palmitate, stearate, isostearate, oleyl oleate, isocetyl stearate, hexyl laurate, dibutyl adipate, dioctyl adipate, myristyl myristate, oleyl erucate, cetyl palmitate, natural oils selected from the group consisting of argan oil, shea butter oil, olive oil, almond oil, avocado oil, ricinus oil, coconut oil, palm oil, sesame oil, peanut oil, whale oil, sunflower oil, peach kernel oil, wheat germ oil, macadamia nut oil, night primrose oil, jojoba oil, castor oil, or soya oil, lanolin, passiflora oil, black cumin oil, borage oil, grapeseed oil, macadamia oil, rosehip oil and hempseed oil, and present at a concentration in the range of 0.01 to 50% by weight calculated to the total of the composition.

11. The composition according to claim 10 wherein Part A comprises argan oil and/or shea butter oil and Part B comprises paraffin oil.

12. The composition according to claim 1 wherein Part A and/or Part B comprises at least one fatty alcohol and at least one non-ionic surfactant.

13. The composition according to claim 1 further comprising one or more of the compounds selected from
cationic polymer,
organic solvent,
coenzyme,
amino acid,
ceramide, and
phytosterol.

14. A kit for dyeing hair comprising at least two compositions wherein one of the compositions is Part A and the other is Part B according to claim 1.

* * * * *